United States Patent [19]
De Simone

[11] Patent Number: 6,166,077
[45] Date of Patent: Dec. 26, 2000

[54] USE OF L-ACETYLCARNITINE, L-ISOVALERYLCARNITINE, L-PROPIONYLCARNITINE FOR INCREASING THE LEVELS OF IGF-1

[75] Inventor: Claudio De Simone, Ardea, Italy

[73] Assignees: Sigma-TAU Industrie Farmaceutiche Riunite S.p.A.; Mendes S.r.l., both of Rome, Italy

[21] Appl. No.: 09/510,672

[22] Filed: Feb. 22, 2000

Related U.S. Application Data

[63] Continuation of application No. 09/147,465, filed as application No. PCT/IT97/00113, May 15, 1997, Pat. No. 6,037,373.

[30] Foreign Application Priority Data

Jul. 5, 1996 [IT] Italy ................................ RM96A0479

[51] Int. Cl.⁷ ................................................. A61K 31/205
[52] U.S. Cl. .......................................................... 514/556
[58] Field of Search ............................................. 514/556

[56] References Cited

U.S. PATENT DOCUMENTS

| | | |
|---|---|---|
| 5,227,518 | 7/1993 | Cavazza . |
| 5,240,961 | 8/1993 | Shug . |
| 5,656,628 | 8/1997 | Weil et al. . |
| 6,037,373 | 3/2000 | De Simone .................... 514/556 |

FOREIGN PATENT DOCUMENTS

| | | |
|---|---|---|
| 0 516 594 A1 | 2/1992 | European Pat. Off. . |
| WO 94/01101 | 1/1994 | WIPO . |
| WO 95/00137 | 1/1995 | WIPO . |

OTHER PUBLICATIONS

Walter G. Sannita et al, "Effects of intravenous L-acetylcarnitine on retinal oscillatory potentials", Documenta Ophthalmologica, vol. 70, 1988, pp. 89–96.

D.J. Paulson et al, "Protection of the ischaemic myocardium by L-propionylcarnitine: effects on the recovery of cardiac output after ischaemia and reperfusion, carnitine transport, and fatty acid oxidation", Cardiovascular Research, vol. 20, 1986, pp. 536–541.

A.J. Liedtke et al, "Effects of L-propionylcarnitine on mechanical recovery during reflow in intact hearts", AM. J. Physiol., vol. 255, No. 1, 1988, pp. H169–H176.

C. Adembri et al, "Ischemia–reperfusion of human skeletal muscle during aortoliliac surgery: effects of acetylcarnitine", Histol Histopath, vol. 9, 1994, pp. 683–690.

J.A. Leipala et al, "Protection of the reperfuse heart by L-propionylcarnitine", J. Applied Physiol., vol. 71, No. 4, 1991, pp. 1518–1528.

Luisa Di Marzio et al, "Acetyl–L–carnitine administration increases insulin–like growth factor 1 levels in asymptomatic HIV–1–infected subjects: correlation with its suppressive effect on lymphocyte apoptosis and ceramide generation", Clinical Immunology, vol. 92, No. 1, 1999, pp. 103–110.

Primary Examiner—Raymond Henley, III
Attorney, Agent, or Firm—Oblon, Spivak, McClelland, Maier & Neustadt, P.C.

[57] ABSTRACT

A method is provided for increasing the levels of IGF-1 for the therapeutic treatment or prophylaxis of cytological disorders or diseases related to IGF-1 selected from the group including neuropathies of the optic nerve and of the olfactory nerve, neuralgia of the trigmeninal nerve, Bell's paralysis, amyotrophic lateral sclerosis, osteoporosis, anthropathy, arthritis, cervical spondylosis and hernia of the intervertebral discs clinical syndromes of reduces height, cachexia and acute or chronic hepatic necrosis, Turner's syndrome, sarcopoenia, growth hormone insensitivity syndromes, obesity, asthenia, myasthenia and heart asthenia, immunodeficiencies and reperfusion injuries, and for the cicatrization of wounds, the healing of ulcers, the treatment of burns, tissue regeneration, cutaneous, intestinal and hepatic tissue regeneration and the formation of dentine, that includes administering, to a patient in need thereof, at least one selected from the group including L-acetylcarnitine, L-isovalerylcarnitine, and L-propionylcarnitine or pharmacologically acceptable salts thereof.

18 Claims, No Drawings

USE OF L-ACETYLCARNITINE, L-ISOVALERYLCARNITINE, L-PROPIONYLCARNITINE FOR INCREASING THE LEVELS OF IGF-1

This is a continuation of U.S. application Ser. No. 09/147,465 filed Jan. 4, 1999, now U.S. Pat. No. 6,037,373 which is a 371 of PCT/IT97/00113 filed May 15, 1997.

The present invention relates to a novel therapeutic use of L-acetylcarnitine, L-isovalerylcarnitine, L-propionylcarnitine or pharmacologically acceptable salts thereof for increasing the levels of IGF-1(insulin-like growth factor 1) for the therapeutic treatment or prophylaxis or cytological disorders or diseases related to IGF-1. More particularly, the present invention relates to the use of L-acetylcarnitine, L-isovalerylcarnitine, L-propionylcarnitine or pharmacologically acceptable salts thereof for the therapeutic treatment or prophylaxis of individuals in whom IGF-1 contributes towards the pathogenesis of a particular disease or provokes cytological disorders.

Like other growth factors, IGF-1 promotes cell growth and differentiation. The administration of IGF-1 obtained as a protein purified by molecular biology methods has made it possible to confirm the effects observed in vitro with cells, on animal models and in man. Essentially, the action of IGF-1 is similar to that of insulin, that is to say an increase in the uptake of glucose, a reduction in ketones and fatty acids in the serum and an increase in protein synthesis. In accordance with these and other metabolic effects, clinical studies have been undertaken in order to evaluate the efficacy of IGF-1 in a range of diseases. IGF-1 has been administered to patients with type-II diabetes, to cachectic patients, to patients with ischemic damage at the neuronal, myocardial or renal level, and ha been proposed for repairing the regenerating tissues (W. L. Lowe, Insulin-like growth factors, Scientific American Science and Medicine p. 62 March 1996).

From the above, it is clear that the administration of IGF-1 may be therapeutically useful in various morbid conditions. Examples of diseases or disorders which may be prevented, cured or improved by the administration of IGF-1 include neuropathies of the optic nerve and of the olfactory nerve, neuralgia of the trigeminal nerve. Bell's paralysis, amyotrophic lateral sclerosis and other motor neuron diseases, degeneration of the retina, osteoporosis, arthropathy, arthritis, cervical spondylosis and hernia of the intervertebral discs, clinical syndromes of reduces height, cachexia, acute or chronic hepatic necrosis. Turner's syndrome, sarcopoenia, growth hormone insensitivity syndromes, diabetes, obesity, asthenia in general and in particular myasthenia and heart asthenia, immunodeficiences and reperfusion injuries. IGF-1 moreover appears to be useful for the cicatrization of wounds, the healing of ulcers, the treatment of burns, tissue regeneration in general and in particular that of cutaneous, intestinal and hepatic tissue, and the formation of dentine.

Unfortunately, the administration of IGF-1 in man brings about undesirable effects such as oedema, pain in the temporomandibular joint and arthralgia. These symptoms are such as to prevent the administration of IGF-1 from being recommended or are responsible for interrupting the treatment. It is therefore necessary to find novel substances which are capable of inducing the production of IGF-1.

According to the present invention, the administration of L-acetylcarnitine, L-isovalerylcarnitine, L-propionylcarnitine or pharmacologically acceptable salts thereof is capable of inducing the production of IGF-1 without the undesirable effects produced by the administration of exogenous IGF-1.

In the description which follows, the expression pharmacologically acceptable salt of L-acetylcarnitine, of L-isovalerylcarnitine or of L-propionylcarnitine is understood to refer to any salt of the above with an acid which does not give rise to undesirable toxicity or side-effects. Such acids are well known to pharmacologists and to experts in the pharmaceutical field.

Non-limiting examples of such salts are: chloride; bromide; iodide; aspartate, in particular hydrogen aspartate; citrate, in particular hydrogen citrate; tartrate; phosphate, in particular hydrogen phosphate; fumarate, in particular hydrogen fumarate; glycero-phosphate, glucose phosphate; lactate; maleate, in particular hydrogen maleate; orotate; oxalate, in particular hydrogen oxalate; sulphate, in particular hydrogen sulphate; trichloroacetate, trifluoroacetate and methanesulphonate.

In the description which follows, for the purposes of brevity and for ease of explanation, reference will be made only to L-acetylcarnitine, it being understood that the description given applies also to the above-mentioned L-isovalerylcarnitine and L-propionylcarnitine and to pharmacologically acceptable salts thereof.

Therapeutic uses of L-acetylcarnitine, L-isovalerylcarnitine and L-propionylcarnitine for the therapeutic treatment of myocardial arrhythmia and ischemia, peripheral functional vasculopathy of the arteries, senile dementia, peripheral neuropathies and myopathies are already previously known. For instance, EP 0 516 594 A1 discloses the use of propionyl- and isovaleryl L-carnitine for treating myopathies, neuronal degeneration and for inhibiting proteolysis. Cardio. Res. 1986, 20:536–541 deals with the protection of the ischaemic myocardium by propionyl L-carnitine. Docum. Ophtal. 1988, 70:89–96 hints at therapeutic potentialities of acetyl L-carnitine in diabetes and diabetic complications of the visual system. However, there is no correlation between these known therapeutic uses and the subject of the present invention.

It has now been found, surprisingly, that L-acetylcarnitine, L-isovalerylcarnitine, L-propionylcarnitine or pharmaceutically acceptable salts thereof are capable of increasing the levels of IGF-1 in human biological fluids. It should be emphasized that, on the basis of extensive supporting scientific literature, the mechanism of action of L-acetylcarnitine has been focused at the metabolic level, more specifically demonstrating a protective action with respect to the mitochondria, whereas the present invention demonstrates an action mediated by the production of IGF-1.

In one embodiment of the present invention, the L-acetylcarnitine, L-isovalerylcarnitine, L-propionylcarnitine or pharmaceutically acceptable salts thereof are administered in combination with vasodilatory, vascular, endocrinological, immunological, cytostatic, immunomodulatory, anti-inflammatory or cortisone pharmaceutical products, IGF-1, IGF-1 binding proteins, growth hormones and other cell growth factors such as, for example, epidermal growth factor, and erythropoietin.

The examples which follow are for the purpose of illustrating the invention and should in no way be understood as implying a limitation in the scope thereof.

EXAMPLE 1

13 individuals infected with HIV were enroled. Blood was taken before and after treatment with L-acetylcarnitine orally at a dosage of 3g/day for 8 weeks. The levels of IGF-1 were measured using a kit supplied by Amersham Italia s.r.l., Milan, and the results were expressed as ng of IGF-1/100 μl of serum.

TABLE 1

| Patient # | Before | After |
|---|---|---|
| 1 | 0.03 | 4.16 |
| 2 | 0.03 | 5 |
| 3 | 0.03 | 0.06 |
| 4 | 0.02 | 5 |
| 5 | 0.02 | 0.05 |
| 6 | 0.04 | 3.25 |
| 7 | 0.25 | 5 |
| 8 | 0.02 | 0.03 |
| 9 | 0.1 | 5 |
| 10 | 0.07 | 5 |
| 11 | 0.03 | 5 |
| 12 | 0.16 | 3.49 |
| 13 | 0.03 | 0.18 |
| AVERAGE | 0.06 | 3.17 |
| Standard deviation | 0.07 | 2.22 |
| Standard error | 0.02 | 0.62 |
| Student test | | 0.0002 |

It is known that individuals infected with HIV can have variable levels of IGF-1 in their serum. The experiments reported here demonstrated that the oral administration of L-acetylcarnitine increases the levels of IGF-1 in peripheral blood.

EXAMPLE 2

Four patients aged above 70 and with healthy dispositions were treated with 2 grams/day of L-acetylcarnitine parenterally for 7 days. The results of the doses of IGF-1 before and after the treatment are reported in Table 2.

TABLE 2

| Patient # | Before | After |
|---|---|---|
| 1 | 0.01 | 2.1 |
| 2 | 0.02 | 3.6 |
| 3 | 0.05 | 1.8 |
| 4 | 0.03 | 3.8 |
| AVERAGE | 0.03 | 2.83 |
| Standard deviation | 0.02 | 1.02 |
| Standard error | 0.008 | 0.51 |
| Student test | | 0.01 |

What is claimed is:

1. A composition, comprising, as active ingredients:
   at least one selected from the group consisting of L-acetylcarnitine, L-isovalerylcarnitine, L-propionylcarnitine and pharmacologically acceptable salts thereof and mixtures thereof; and
   at least one selected from the group consisting of L-carnitine, coenzyme Q10, vitamin E and Se-L-methionine and pharmaceutically acceptable salts and derivatives thereof and mixtures thereof.

2. The composition of claim 1, comprising L-carnitine or a pharmacologically acceptable salt thereof.

3. The composition of claim 1, comprising coenzyme Q10.

4. The composition of claim 1, comprising vitamin E.

5. The composition of claim 1, comprising Se-L-methionine or a pharmacologically acceptable salt thereof.

6. The composition of claim 1, comprising L-acetylcarnitine, L-isovalerylcarnitine, L-propionylcarnitine and/or pharmacologically acceptale salts thereof.

7. The composition of claim 1, comprising L-acetylcarnitine or a pharmacologically acceptable salt thereof.

8. The composition of claim 1, comprising L-isovalerylcarnitine or a pharmacologically acceptable salt thereof.

9. The composition of claim 1, comprising L-propionylcarnitine or a pharmacologically acceptable salt thereof.

10. A pharmaceutical composition, comprising the composition of claim 1, and a pharmaceutically acceptable excipient.

11. A method for increasing the level of IGF-1 for the therapeutic treatment or prophylaxis of cytological disorders or diseases related to IGF-1 selected from the group consisting of neuropathies of the optic nerve and of the olfactory nerve, neuralgia of the trigeminal nerve, Bell's paralysis, amyotrophic lateral sclerosis, osteoporosis, arthropathy, arthritis, cervical spondylosis and hernia of the intervertebral discs, clinical syndromes of reduced height, cachexia and acute or chronic hepatic necrosis. Turner's syndrome, sarcopoenia, growth hormone insensitivity syndromes, obesity, asthenia, myasthenia and heart asthenia, immunodeficiencies and reperfusion injuries, and for the cicatrization of wounds, the healing of ulcers, the treatment of burns, tissue regeneration, cutaneous, intestinal and hepatic tissue regeneration and the formation of dentine, comprising administering to a patient in need thereof a composition, comprising, as active ingredients:
   at least one selected from the group consisting of L-acetylcarnitine, L-isovalerylcarnitine, L-propionylcarnitine and pharmacologically acceptable salts thereof and mixtures thereof; and
   at least one selected from the group consisting of L-carnitine, coenzyme Q10, vitamin E and Se-L-methionine and pharmaceutically acceptable salts and derivatives thereof and mixtures thereof.

12. A method for treating HCV, comprising administering to a patient in need thereof a composition, comprising, as active ingredients:
   at least one selected from the group consisting of L-acetylcarnitine, L-isovalerylcarnitine, L-propionylcarnitine and pharmacologically acceptable salts thereof and mixtures thereof; and
   at least one selected from the group consisting of L-carnitine, coenzyme Q10, vitamin E and Se-L-methionine and pharmaceutically acceptable salts and derivatives thereof and mixtures thereof.

13. The composition of claim 1, which is suitable for the oral, parenteral, nasal or topical administration of 0.01 mg-15 g per day of active ingredients.

14. The composition of claim 1, which is suitable for the oral, parenteral, nasal or topical administration 0.1 mg - 10 g per day of active ingredients.

15. The method claim 11, wherein 0.01 mg-15 g per day of active ingredients are administered.

16. The method of claim 11, wherein 0.1 mg-10 g per day of active ingredients are administered.

17. The method of claim 12, wherein 0.01 mg-15 g per day of active ingredients are administered.

18. The method of claim 12, wherein 0.1 mg-10 g per day of active ingredients are administered.

* * * * *